US007488821B2

(12) United States Patent
Rao et al.

(10) Patent No.: US 7,488,821 B2
(45) Date of Patent: Feb. 10, 2009

(54) POLYMORPH OF QUETIAPINE FUMARATE AND A PROCESS FOR ITS PREPARATION

(75) Inventors: Mysore Aswatha Rao, Andhra Pradesh (IN); Srinivasan Subramanian Kuduva, Andhra Pradesh (IN); Mellekatte Thimmesh Shreenivas, Andhra Pradesh (IN)

(73) Assignee: Divi's Laboratories Limited, Hyderabad (IN)

( * ) Notice: Subject to any disclaimer, the term of this patent is extended or adjusted under 35 U.S.C. 154(b) by 639 days.

(21) Appl. No.: 11/268,947

(22) Filed: Nov. 8, 2005

(65) Prior Publication Data

US 2006/0223994 A1 Oct. 5, 2006

(30) Foreign Application Priority Data

Apr. 4, 2005 (IN) .......................... 361/CHE/2005

(51) Int. Cl.
*C07D 281/02* (2006.01)

(52) U.S. Cl. ...................................................... 540/551

(58) Field of Classification Search .................. 540/551
See application file for complete search history.

(56) References Cited

U.S. PATENT DOCUMENTS

| | | | |
|---|---|---|---|
| 4,879,288 | A | 11/1989 | Warawa et al. |
| 2003/0216376 | A1 | 11/2003 | Lifshitz-Liron et al. |

FOREIGN PATENT DOCUMENTS

| | | |
|---|---|---|
| WO | WO 2004/078735 | 9/2004 |

OTHER PUBLICATIONS

Polymorphism: A pharmaceutical Science Perspective, Hancock, B.C., Shalaev, E.Y.; Shamblin, S.L. J. Pharm. Pharmacol, 54:1151-1152, (2002).
ICH guidelines for residual solvents, Q3C, 1997, (Federal Register, vol. 68, No. 219, Thursday, Nov. 13, 2003; pp. 64352-64353.
CRC Handbook of Laboratory Safety, Edited by A. Keith Furr, CRC Press, Boca Raton, 4th Edition, 1995, p. 217-564 (Attached only related pages (2).
Merck Index, Merck & Co. Inc. USA, Entry 2160, 13th Edition, 2001.
Angell, C.A., Sare, E. J., J. Chem, Phys 52: 1058-1068 (1970).

*Primary Examiner*—Brenda L Coleman
(74) *Attorney, Agent, or Firm*—Caesar, Rivise, Bernstein, Cohen & Pokotilow, Ltd.

(57) ABSTRACT

The present invention relates to a novel polymorph of Quetiapine fumarate and a simple method for its preparation.

8 Claims, 3 Drawing Sheets

DIVTS LABS,(R&D)-SANATHNAGAR
PM-210-1
(Melted)
666.92
742.17
763.49
996.85
1062.35
1121.72
1246.36
1303.16
1383.15
1455.93
1574.32
1600.41
190372
2316.11
2858.32
3388.53
%T
52.3
50
48
46
44
42
40
38
36
34
32
30
28
26
24.0
4000.0
3000
2000
1500
1000
450.0
cm-1

QTP. tlf-Melt
PM-210-1,14.12.004 10:22:25
PM-210-1,4.9000 mg
Method: PM-R
30.0-200.0°C2.00°C/min N2 -50.0ml/min
200.0 -30.0°C-2.00°C/min N2 -50.0ml/min
Integral 352.09 MJ
Nomalized 71.85 JG^-1
Onset 162.54°C
Peak 167.15°C
Endset 170.19°C
Heating rate 2.00. Cmin^-1
Integral 1.65 MJ
Nomalized 0.34 JG^-1
Onset 200.03°C
Peak 199.88°C
Endset 199.77°C
Heating rate -2.00. Cmin^-1
Integral 3.95MJ
Nomalized 0.81 JG^-1
Onset 144.21°C
Peak 144.37°C
Endset 144.95°C
Heating rate 2.00.°Cmin^-1
mW
0.5
0.0
-0.5
-1.0
-1.5
-2.0
50 100 150 200 150 100 50 °C
0 20 40 60 80 100 120 140 180 min

POLYMORPH OF QUETIAPINE FUMARATE AND A PROCESS FOR ITS PREPARATION

CROSS-REFERENCE TO RELATED APPLICATION

This application claims the benefit of the filing date of Application 361/CHE/2005, filed on Apr. 4, 2005, the entire disclosure of which is incorporated by reference herein.

BACKGROUND OF THE INVENTION

1. Field of Invention

The present invention relates to a novel polymorph of Quetiapine fumarate and a process for its preparation. The novel polymorph of quetiapine fumarate of the present invention has been designated by us as Form IV. The quetiapine fumarate is salt of 2-[2-(4-dibenzo [b,f]][1,4] thiazepin-11-yl-1-piperazinyl) ethoxy]-ethanol with fumaric acid (2:1). It is also referred as hemifumarate in some patent literature. Its complete structure is shown below:

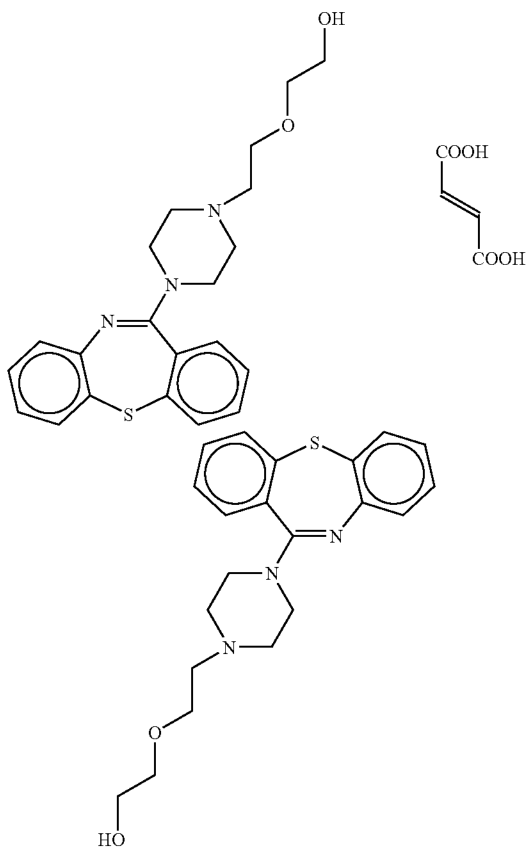

Quetiapine fumarate is a well known anti psychotic agent useful in treating schizophrenia and other CNS disorders.

2. Description of Related Art

U.S. Pat. No. 4,879,288 discloses a process for the preparation of Quetiapine hemifumarate. According to this patent, a crystalline quetiapine hemifumarate is prepared by treating ethanolic solution of Quetiapine free base with fumaric acid. The compound was characterized only by its melting point (172-173° C.) and C,H,N analysis. No other characteristics have been described in the '288 patent. However, the authors of a later patent application US 2003/0216376 have prepared the same compound by the method described in the '288 patent and characterized the same additionally with XRD and FT-IR data, at the same time designating it as Form I. Although the '376 application is accompanied by FIGS. (9 & 10) of XRD and FTIR of the "Form I", data are not quoted by the authors. Our attempt to produce the crystalline form of quetiapine hemifumarate as described in '288' patent and showing characteristics of "Form I" failed. The XRD and FT-IR data of the product prepared by the above mentioned process, from several experiments confirmed that the procedure described in '288 patent does not yield consistent product.

U.S. Patent Application No. 2003/0216376A1 describes two new polymorphs of quetiapine hemifumarate besides their solvate forms. The two new polymorphs are designated Forms II and III by the authors.

Form II is prepared by treating quetiapine hemifumarate with chlorinated solvents. Form II solvate of chloroform is obtained when the chlorinated solvent is chloroform and Form II solvate of methylene chloride is obtained when the chlorinated solvent is methylene chloride.

Form III is prepared by treating quetiapine hemifumarate solution in an aprotic solvent with chloroform and stirring the resulting mixture for a period of at least 14 hours. Form III is obtained as solvate of chloroform.

The characteristics of the two new forms II and III as given in the '376 patent application are shown in table I below:

TABLE I

| | XRD −2θ Values | FT - IR $cm^{-1}$ | DSC peaks° C. |
|---|---|---|---|
| Form II ('376) | 7.8, 11.9, 12.5 15.7, 23.0, 23.4 | 639, 1112, 1395, 1616, 1711, 3423 | 130 and 166 |
| Form III ('376) | 8.9, 11.8, 15.3 19.4, 23.0, 23.4 | 748, 758, 1402, 1607, 1715, 2883 | 111, 142 and 167 |

Only the '288 patent and '376 patent application refer to the compound as 'hemifumarate' salt whereas all other standard literature refer it simply as "fumarate." In the rest of this document the name "quetiapine fumarate" is retained and is inclusive of the alternate name of "quetiapine hemifumarate."

WO 2004/078735 also describes two new crystalline polymorphs of quetiapine fumarate, characterized by its XRD pattern. The U.S. Patent Application No. US 2003/0216376A1 was filed on Mar. 20, 2003 and published on Nov. 20, 2003. WO 2004/078735 was filed on Mar. 3 ,2003 before the publication of the '376 application. The authors of the '735 patent application have also chosen to name their new polymorphs as "Form I and II." This has led to some confusion. However, the '735 forms I and II clearly differ from the '376 forms II and III. The '735 application records only the XRD data of the "Forms I & II". The data given in the '735 application is shown below in table II. Neither the FT-IR nor the DSC data for these new forms are provided.

TABLE II

XRD Data (2θ values) as given in '735 patent application

| Form I | Form II |
|---|---|
| 7.3, 9.2, 11.6, 13.3, 14.4, 14.8, 15.3, 15.9, 16.2, 16.7, 17.6, 19.1, 19.7, 20.1, 20.8, 21.1, 21.8, 22.3, 23.4, 24.3, 24.7, 25.1, 25.6, 27.1, 28.5, 29.5, 33.2 and 40.4 | 4.9, 7.4, 9.2, 11.7, 13.4, 14.4, 14.9, 15.4, 15.9, 16.3, 16.7, 17.7, 18.6, 19.8, 20.2, 20.8, 21.2, 21.9, 22.4, 22.9, 23.4, 24.3, 24.7, 25.2, 25.7, 26.9, 27.8, 28.8, 29.4, 33.2, 35.9, 38.0, 38.7, 39.9 and 42.8 |

According to WO 2004/078735, Form I is prepared by dissolving quetiapine free base and fumaric acid in a suitable solvent such as acetone, isobutyl ketone, ethyl acetate, ethyl formate, or methyl acetate by heating. On cooling the solution to about 25° C., crystals of Form I are obtained.

Form II is obtained by dissolving quetiapine in methyl tert.butyl ether and adding fumaric acid to the quetiapine solution at reflux temperature. On cooling the solution to about 25° C., crystals of Form II are obtained.

Form I and Form II obtained by the methods described in '735 application seem to differ from the Forms II and III obtained according to the US patent application Ser. No. US 2003/0216376A1 in their XRD patterns.

In addition to the two new crystalline polymorphs the PCT application No. WO 2004/078735 also describes an amorphous form of quetiapine fumarate. The authors have not designated it by any trivial name but refer to it simply as "amorphous form." It is obtained by dissolving quetiapine fumarate in a solvent mixture containing methanol and chloroform and vacuum drying, as per the '735 application.

The amorphous form is characterized by powder XRD pattern having maximum expressed as 2θ at about 10° to about 30°. The accompanying diagram in the patent application displays a series of maxima as claimed.

All the existing polymorphs, as explained above, are obtained using chlorinated solvents such as chloroform and methylene chloride. Both chloroform and methylene chloride are known carcinogens (CRC Handbook of Laboratory Safety, Edited by A. Keith Furr, CRC Press, Boca Raton, 4th Edition, 1995, pg 217-564). (Merck Index, Merck & Co. Inc, USA, Entry 2160, 13th Edition, 2001) Chloroform is also banned by FDA from use in drug, cosmetic, and food packaging products. Both chloroform and methylene chloride are designated as Class 2 solvents under International Conference on Harmonisation (ICH) because of their inherent toxicity. (ICH guidelines for residual solvents, 1997).

The solvate polymorphs of Forms II and III obtained as per the U.S. Patent Application No. U.S. 2003/0216376A1 contain chlorinated solvents, hence hazardous to health. The amorphous form of Quetiapine fumarate prepared by the method of WO 2004/078735 also uses the undesirable chloroform.

All references cited herein are incorporated herein by reference in their entireties.

BRIEF SUMMARY OF THE INVENTION

Quetiapine fumarate is an important anti-dopaminergic compound and is useful as an antipsychotic and neuroleptic drug. There is a need to develop a process for the preparation of polymorphic forms of quetiapine fumarate without employing hazardous chlorinated hydrocarbon solvents which are known carcinogens and are controlled very stringently by regulatory bodies like the ICH, EDQM, FDA etc.

Accordingly an improved process was developed for the preparation of quetiapine fumarate without employing hazardous chlorinated hydrocarbon solvents. Such a process would be very useful for commercial production of the important drug quetiapine fumarate without creating any environmental problems and would also be safe. The present invention surprisingly resulted in preparing an entirely new polymorph of quetiapine fumarate which we have designated as Form IV.

Therefore the main objective of the present invention is to provide a novel polymorph of quetiapine fumarate designated as Form IV having the characteristics different from the hitherto known polymorphic forms of quetiapine fumarate and having an acceptable stability when subjected to pharmaceutical operations like grinding or size reduction employed in the manufacture of dosage forms.

Another objective of the present invention is to provide a process for the preparation of a novel polymorph of quetiapine fumarate designated as Form IV having the characteristics different from the hitherto known polymorphic forms of quetiapine fumarate without using any solvents especially the hazardous chlorinated solvents.

Still another objective of the present invention is to provide a process for the preparation of a novel polymorph of quetiapine fumarate designated as Form IV having the characteristics different from the hitherto known polymorphic forms of quetiapine fumarate, which is safe, environmentally friendly and commercially viable.

Yet another objective of the present invention is to provide a process for the preparation of a novel polymorph of quetiapine fumarate designated as Form IV having the characteristics different from the hitherto known polymorphic forms of quetiapine fumarate the preparation of which is simple and economical.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

The occurrence of more than one amorphous form, described as "polyamorphism," is well documented in the literature. (Hancock, B. C. et al. (2002). *J. Pharm. Pharmacol.* 54:1151-1152; Angell, C. A., Sare, E. J. (1970). *J. Chem. Phys* 52: 1058-1068).

Figure 1:
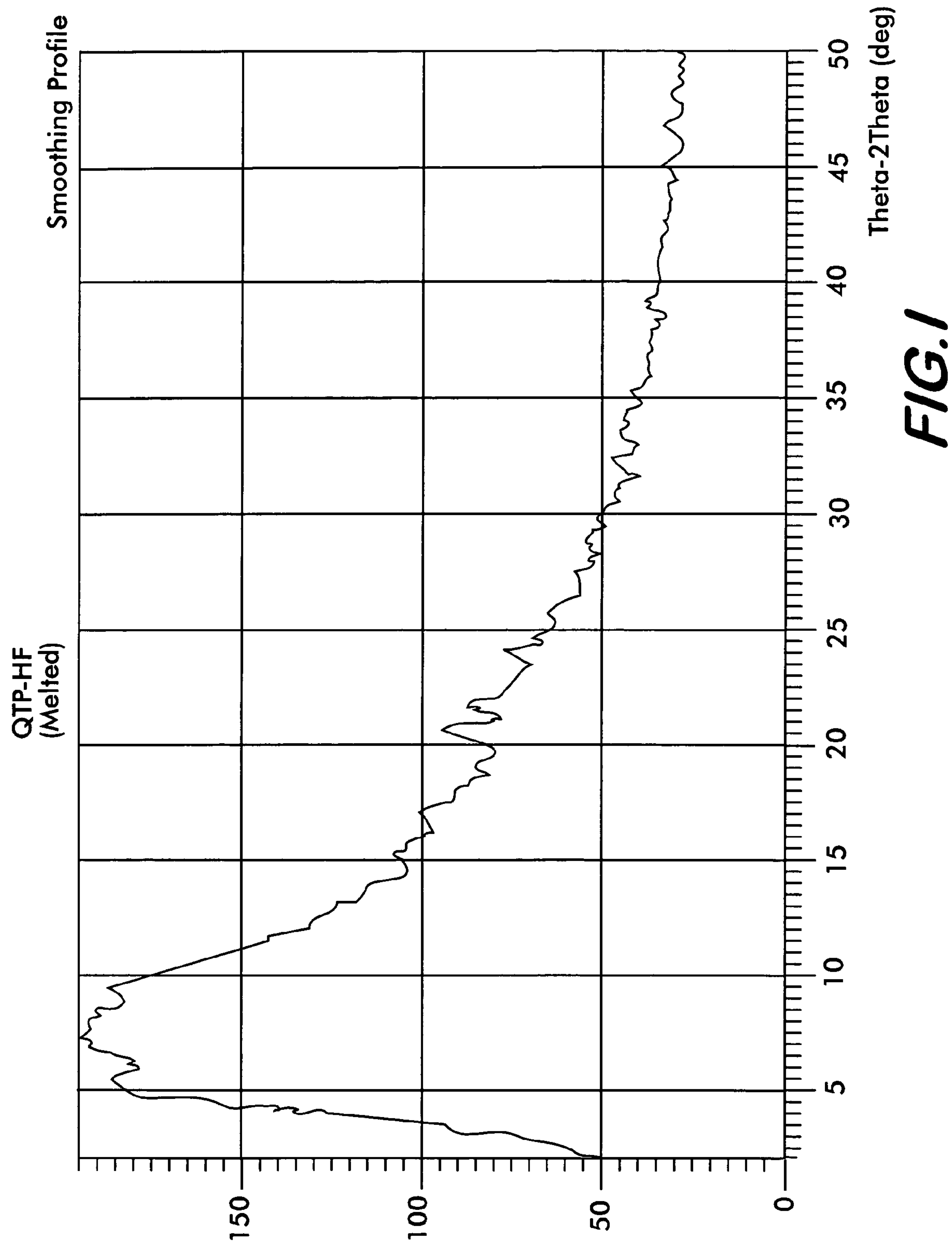
FIG. 1 is an XRD trace of Quetiapine fumarate.

The novel form IV of the present invention is characterized by the X-ray diffraction pattern of a plain halo as given in FIG. 1 of the drawing accompanying this specification and does not exhibit any maxima between about 10° and about 30° 2θ values.

The XRD pattern clearly shows that the present amorphous form is different from that described in WO 2004/078735. As mentioned earlier the "735" application describes an amorphous form, characterized by powder XRD pattern having maximum expressed as 2θ at about 10° to about 30°. The Form IV obtained by the process of the present invention is free from such characteristic maxima as can be seen from the FIG. 1.

Figure 2:
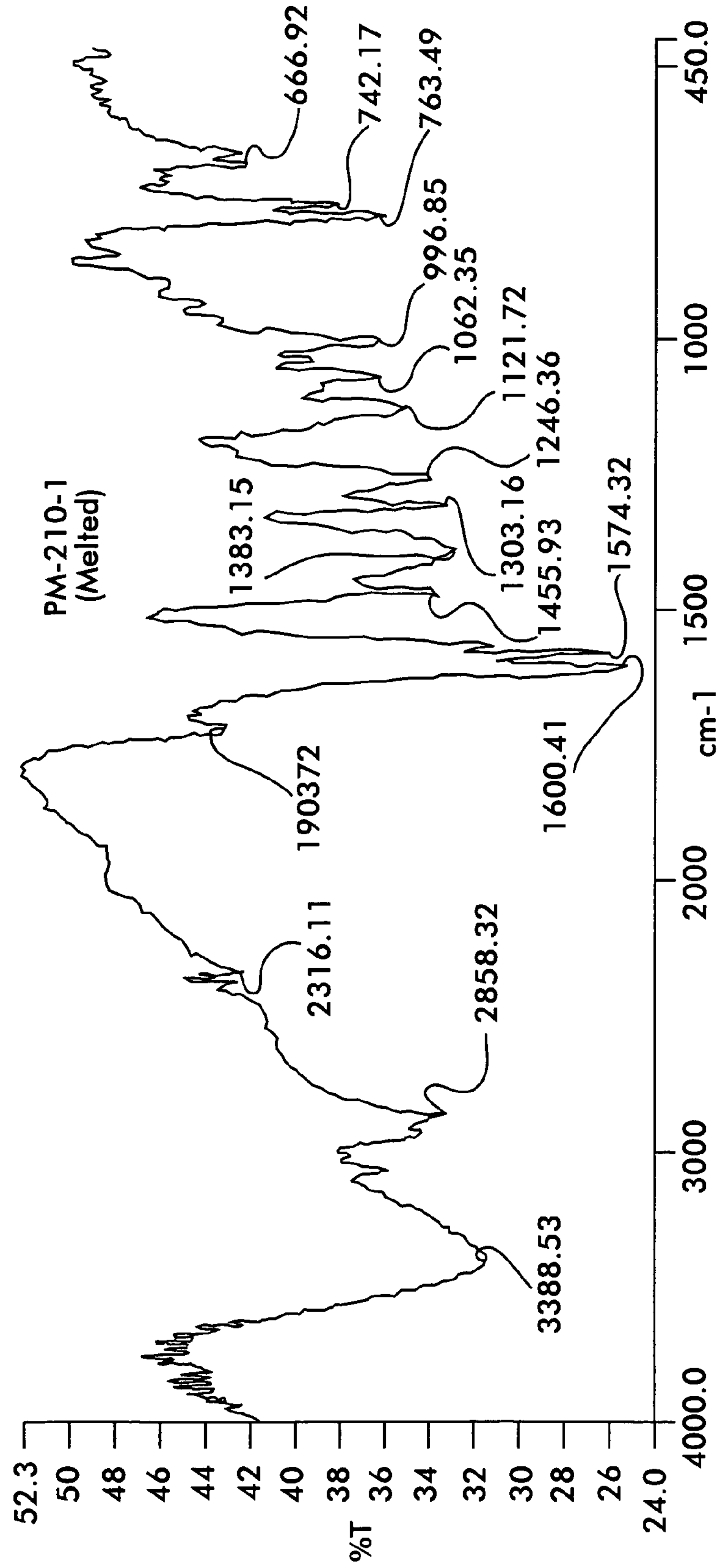
FIG. 2 is an IR-Spectrum of Quetiapine fumarate.

The novel amorphous form of the present invention is also characterized by FTIR which exhibits peaks at about 3321, 3050, 2867, 1718, 1599, 1573, 1457, 1413, 1336, 1305, 1244, 1121, 1063, 1014, 997, 926, 835, 813, 794, 766, 668 and 466 $cm^{-1}$ as shown in FIG. 2. The '735' application does not disclose the FTIR spectrum for the amorphous form.

Accordingly the present invention provides a novel polymorph of quetiapine fumarate designated as Form IV having the characteristic X-ray diffraction pattern of a plain halo between about 10° to 50° of 2θ values (FIG. 1) and an FTIR spectrum (FIG. 2) showing peaks at about 3321, 3050, 2867, 1718, 1599, 1573, 1457, 1413, 1336, 1305, 1244, 1121, 1063, 1014, 997, 926, 835, 813, 794, 766, 668, 466 $cm^{-1}$ respectively. The plain halo between about 10° to 50° of 2θ values does not exhibit any distinct maxima.

The XRD pattern in respect of Form IV (FIG. 1) clearly shows that the present amorphous form is different from that described in WO 2004/078735 . As mentioned earlier, the "735" application describes an amorphous form, characterized by powder XRD pattern having maximum expressed as 2θ at about 10° to about 30°. The Form IV obtained by the process of the present invention is free from such characteristic maxima as can be seen from FIG. 1.

The novel amorphous form of the present invention is also characterized by FTIR which exhibits peaks at about 3321, 3050, 2867, 1718, 1599, 1573, 1457, 1413, 1336, 1305, 1244, 1121, 1063, 1014, 997, 926, 835, 813, 794, 766, 668 and 466 $cm^{-1}$ as shown in FIG. 2. The '735' application does not disclose the FTIR spectrum for the amorphous form.

According to another embodiment of the present invention there is provided a process for the preparation of novel polymorph of quetiapine fumarate designated as Form IV having the characteristics given above which comprises heating quetiapine fumarate until it melts either by using normal pressure or reduced pressure followed by cooling till it solidifies. The melting temperature is governed by the pressure employed. For example at 2 mm Hg pressure the compound melts at about 110° C. itself, whereas at normal pressure of 760 mm Hg it melts at about 170° C. The resultant solid is removed and ground to obtain a colorless amorphous powder to obtain the novel amorphous solid form IV.

Quetiapine fumarate used in the process of the present invention can be prepared as described in U.S. Pat. No. 4,879,288 or by any other suitable method. As per '288 patent, quetiapine free base was dissolved in ethanol and then treated with furmaric acid. The reaction mixture was warmed to obtain a clear solution. After one hour at room temperature, the salt quetiapine fumarate precipitates out, which was filtered and dried.

The sample of quetiapine fumarate prepared as above is heated directly in a suitable vessel, without any solvent, till it melts either by using normal pressure or reduced pressure. The heating is preferably done at the rate of 10° C./min. The molten liquid is cooled to ambient temperature. The cooling is done either slowly by keeping at room temperature (examples 1 to 4) or cooled rapidly by immersing the vessel at 0° C. (example 5). In either case the salt solidifies to a novel amorphous solid. The resultant solid is removed and ground to obtain a colorless amorphous powder.

Quetiapine fumarate prepared as described in U.S. Pat. No. 4,879,288 melts at 170 to 172° C. at normal pressure. The melt temperature can be decreased if so desired by reducing the pressure (Examples 3 and 4).

The melting and cooling can be done in air or preferably under an inert atmosphere like nitrogen atmosphere, to prevent any oxidative degradation, although no significant degradation was observed in air. The melting temperature, pressure and rate of cooling do not affect the product, whose XRD and the FTIR characteristics remain unaltered. Heating does not also alter its chemical nature as confirmed by NMR, IR, and by comparing the retention time and assay by HPLC with the sample prepared as described in U.S. Pat. No. 4,879,288 or by any other suitable method. The sample remains stable in terms of all the characteristics described for form IV even after subjecting to prolonged grinding for example in a mortar with pestle.

The details of the present invention are described in the Examples given below which are provided to illustrate the invention only and should not be construed to limit the scope of the present invention in any way.

EXAMPLE-1

Figure 3:
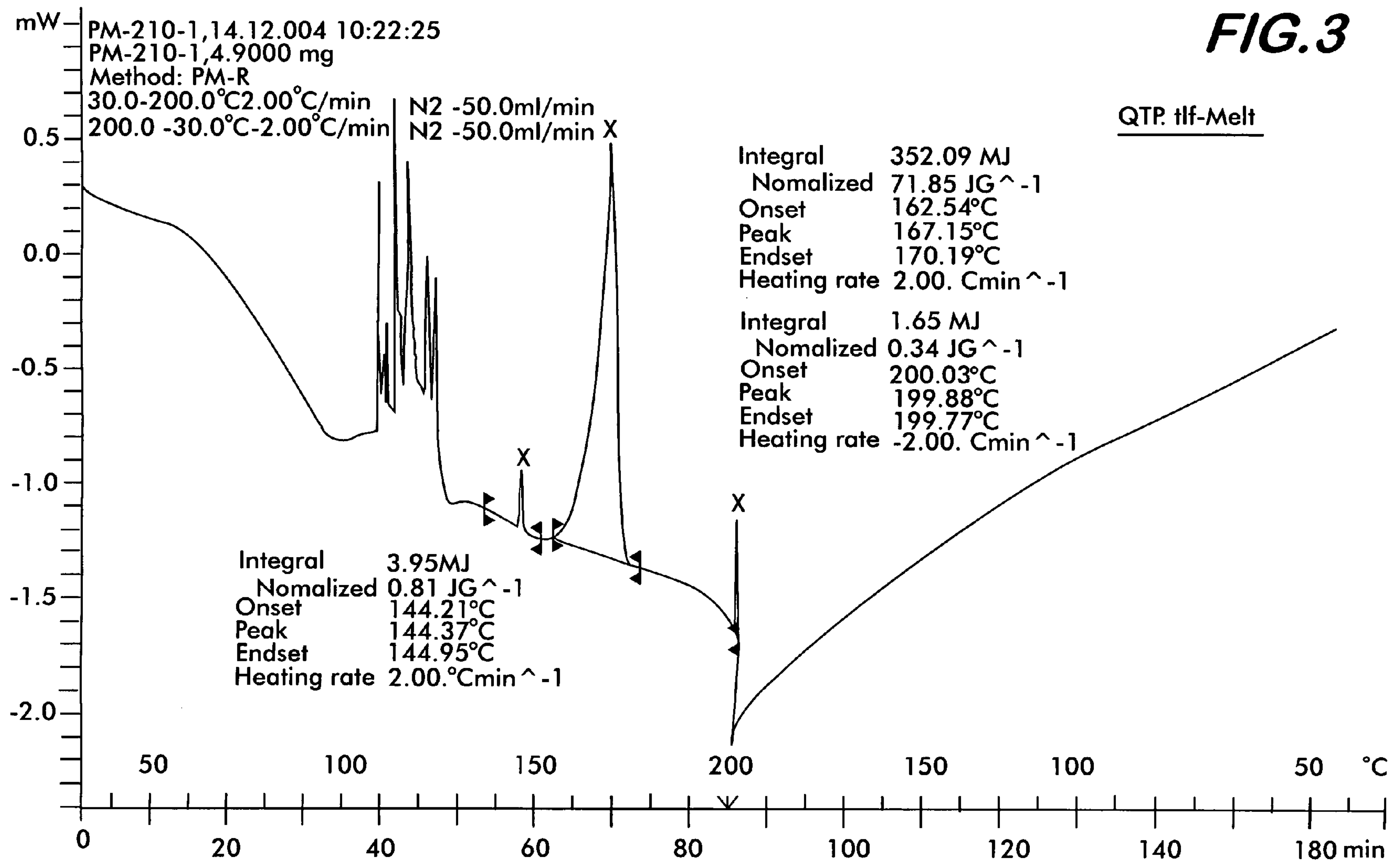
FIG. 3 is a DSC of Quetiapine fumarate.

Quetiapine fumarate (1 g) is taken in a RB flask and heated at a rate of 10° C. per minute. At about 170° C., the material melts into a clear liquid. Heating is discontinued after all the sample melts completely and the flask is allowed to cool at room temperature till the melt solidifies. The resultant solid is removed and ground to obtain a colorless amorphous powder This is the novel Form IV (Yield: 0.98 g) which shows characteristic XRD pattern as shown in FIG. 1, FTIR as shown in FIG. 2, and DSC thermogram as shown in FIG. 3.

EXAMPLE-2

Quetiapine fumarate (1 g) is taken in a RB flask and flushed with nitrogen. The flask is heated at a rate of 10° C. per minute under a stream of nitrogen. At about 170° C., the material melts into a clear liquid. Heating is discontinued after all the sample melts completely and the flask is allowed to cool at room temperature till the melt solidifies. The resultant solid is removed and ground to obtain a colorless amorphous powder of novel form IV (Yield: 0.99 g) which shows characteristic XRD pattern as shown in FIG. 1, FTIR as shown in FIG. 2.

EXAMPLE-3

Quetiapine fumarate (1 g) is taken in a RB flask and the flask is evacuated slowly to 2.0 mm Hg pressure. The flask is heated at a rate of 10° C. per minute. At about 110° C., the material melts into a clear liquid. Heating is discontinued after all the sample melts completely and the flask is allowed to cool at room temperature till the melt solidifies and the vacuum released. The resultant solid is removed and ground to obtain a colorless amorphous powder of novel form IV (Yield: 0.98 g) which shows characteristic XRD pattern as shown in FIG. 1, FTIR as shown in FIG. 2.

EXAMPLE-4

Quetiapine fumarate (1 g) is taken in a RB flask and the flask is evacuated slowly to 0.2 mm Hg pressure. The flask is heated at a rate of 10° C. per minute. At about 110° C., the material melts into a clear liquid. Heating is discontinued after all the sample melts completely and the flask is allowed to cool at room temperature till the melt solidifies and the vacuum released. The resultant solid is removed and ground to obtain a colorless amorphous powder of novel form IV (Yield: 0.97 g) which shows characteristic XRD pattern as shown in FIG. 1, and FTIR as shown in FIG. 2.

EXAMPLE-5

Quetiapine fumarate (1 g) is taken in a RB flask and the flask is heated at a rate of 10° C. per minute. At about 170° C., the material melts into a clear liquid. Heating is discontinued after all the sample melts completely. The flask is rapidly cooled to 0° C. by immersing the flask into crushed ice. The solid obtained is removed and ground to obtain a colorless amorphous powder of the novel from IV (Yield: 0.97 g) which shows characteristic XRD pattern as shown in FIG. 1, and FTIR as shown in FIG. 2.

EXAMPLE-6

Quetiapine fumarate (1 g) obtained according to example-1 was taken in a clean glass pestle and mortar and ground for 15 min. and the resulted solid analyzed by powder XRD and FT-IR. The XRD pattern and FT-IR spectrum of the resultant material is identical to the form IV. Duration and force of grinding did not alter the nature of the material.

ADVANTAGES OF THE INVENTION

1. Results in a novel amorphous form, Form IV of quetiapine fumarate.
2. The process for making the novel Form IV is extremely simple and does not use any solvent, especially hazardous chlorinated solvents.
3. The process of preparing the novel Form IV is easy and is not affected by melting temperature or pressure used in the process
4. The novel form IV is stable under prolonged grinding or micronisation, a step often incorporated during manufacture of dosage forms like tablets and capsules.

While the invention has been described in detail and with reference to specific examples thereof, it will be apparent to one skilled in the art that various changes and modifications can be made therein without departing from the spirit and scope thereof.

What is claimed is:

1. An novel amorphous form IV of quetiapine fumarate having the characteristic X-ray diffraction pattern of a plain halo between about 10 to 50° of 2θ values and an FTIR spectrum showing peaks at about 3321, 3050, 2867, 1718, 1599, 1573, 1457, 1413, 1336, 1305, 1244, 1121, 1063, 1014, 997, 926, 835, 813, 794, 766, 668 and 466 $cm^{-1}$.

2. A process for the preparation of an amorphous form IV of quetiapine fumarate having the characteristics as in claim 1, which comprises heating quetiapine fumarate until it melts either at normal pressure or at reduced pressure, followed by cooling till it solidifies.

3. A process as claimed in claim 2 wherein the heating is carried out under reduced pressure between 0.2 mm and 760.0 mm Hg.

4. A process as claimed in claims 2 wherein the heating is carried out in an inert atmosphere using an inert gas.

5. A process as claimed in claims 3 wherein the heating is carried out in an inert atmosphere using an inert gas.

6. The process of claim 4 wherein the inert gas is nitrogen or argon.

7. The process of claim 5 wherein the inert gas is nitrogen or argon.

8. A process as claimed in any one of claims 2 to 4 wherein the melt obtained is cooled rapidly at about 0° C., or slowly at ambient temperature.

* * * * *